(12) United States Patent
Yoshizawa et al.

(10) Patent No.: US 8,406,846 B2
(45) Date of Patent: Mar. 26, 2013

(54) MAMMOGRAPHIC APPARATUS

(75) Inventors: Mayuka Yoshizawa, Kyoto (JP);
Masami Maekawa, Kyoto (JP); Keishi Kitamura, Kyoto (JP); Ichiro Oda, Kyoto (JP); Koji Shimizu, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1150 days.

(21) Appl. No.: 12/295,265

(22) PCT Filed: Mar. 20, 2007

(86) PCT No.: PCT/JP2007/055721
§ 371 (c)(1),
(2), (4) Date: Sep. 29, 2008

(87) PCT Pub. No.: WO2007/119459
PCT Pub. Date: Oct. 25, 2007

(65) Prior Publication Data
US 2010/0234727 A1    Sep. 16, 2010

(30) Foreign Application Priority Data

Mar. 31, 2006   (JP) ................................ 2006-099005

(51) Int. Cl.
*A61B 5/05*   (2006.01)
(52) U.S. Cl. ........................ 600/407; 600/410
(58) Field of Classification Search .......... 600/407–429, 600/473–480, 437–469; 378/37, 167, 177–179, 378/193–198
See application file for complete search history.

(56) References Cited

U.S. PATENT DOCUMENTS

| 4,433,690 | A | * | 2/1984 | Green et al. .................. 600/448 |
| 5,029,193 | A | * | 7/1991 | Saffer ............................. 378/37 |
| 5,305,365 | A |   | 4/1994 | Coe |
| 5,386,447 | A |   | 1/1995 | Siczek |
| 5,584,292 | A | * | 12/1996 | Cheung ......................... 600/567 |

(Continued)

FOREIGN PATENT DOCUMENTS

| DE | 2014 151 A1 | 12/1971 |
| JP | 51-028065 U | 3/1976 |

(Continued)

OTHER PUBLICATIONS

Ribeiro, R. et al., "Breast Imaging with a Dedicated PEM", Nuclear Instruments and Methods in Physics Research A, 2004, vol. 527, pp. 87-91.

(Continued)

*Primary Examiner* — Sanjay Cattungal
(74) *Attorney, Agent, or Firm* — Cheng Law Group, PLLC

(57) ABSTRACT

The mammographic apparatus of this invention maintains peripheral portions of the breast area Ma of the sternal plate of a patient M in contact with a sternal plate contact box 3 during radiography for RI distribution images of the breast area Ma of the patient M. Since the body motion accompanying respiration of the patient M shifts from the breast side to the back side, the motion of the breast area Ma of the patient M accompanying respiration of the patient M is suppressed easily. In addition, since radiography for RI distribution images is carried out with the patient M in a seated position seated on a seating unit 2, the apparatus is compact and can installed in a limited area, compared with an apparatus that carries out radiography for RI distribution images with a patient in a sleeping position lying on her back or on a side on a top board.

24 Claims, 13 Drawing Sheets

U.S. PATENT DOCUMENTS

| | | | |
|---|---|---|---|
| 5,719,398 A * | 2/1998 | Colak | 250/341.1 |
| 5,820,552 A * | 10/1998 | Crosby et al. | 600/407 |
| 5,820,558 A * | 10/1998 | Chance | 600/473 |
| 5,825,910 A * | 10/1998 | Vafai | 382/132 |
| 5,833,627 A * | 11/1998 | Shmulewitz et al. | 600/562 |
| 5,999,836 A * | 12/1999 | Nelson et al. | 600/407 |
| 6,429,432 B1 * | 8/2002 | McNaught et al. | 250/363.02 |
| 6,498,942 B1 * | 12/2002 | Esenaliev et al. | 600/310 |
| 6,504,157 B2 * | 1/2003 | Juhi | 250/363.04 |
| 6,525,320 B1 * | 2/2003 | Juni | 250/363.04 |
| 6,525,321 B2 * | 2/2003 | Juni | 250/363.04 |
| 6,542,772 B1 * | 4/2003 | Chance | 600/473 |
| 6,748,044 B2 | 6/2004 | Sabol et al. | |
| 6,795,195 B1 * | 9/2004 | Barbour et al. | 356/446 |
| 6,848,826 B2 * | 2/2005 | Marie et al. | 378/196 |
| 6,860,855 B2 * | 3/2005 | Shelby et al. | 600/459 |
| 6,873,716 B1 * | 3/2005 | Bowker et al. | 382/128 |
| 7,379,769 B2 * | 5/2008 | Piron et al. | 600/415 |
| 7,609,808 B2 * | 10/2009 | Tornai et al. | 378/63 |
| 7,627,365 B2 * | 12/2009 | Chance | 600/475 |
| RE41,949 E * | 11/2010 | Barbour et al. | 356/446 |
| 8,027,711 B2 * | 9/2011 | Jones et al. | 600/407 |
| 2002/0122533 A1 * | 9/2002 | Marie et al. | 378/196 |
| 2005/0010114 A1 | 1/2005 | Porath | |
| 2006/0173307 A1 * | 8/2006 | Amara et al. | 600/437 |
| 2006/0241727 A1 * | 10/2006 | Dowlatshahi | 607/89 |
| 2007/0237306 A1 * | 10/2007 | Jones et al. | 378/195 |
| 2008/0004526 A1 * | 1/2008 | Gross | 600/437 |
| 2008/0103387 A1 * | 5/2008 | Gross | 600/424 |

FOREIGN PATENT DOCUMENTS

| | | |
|---|---|---|
| JP | 2000-075035 A | 3/2000 |
| JP | 2000-214263 A | 8/2000 |
| JP | 2002-102215 A | 4/2002 |
| JP | 2002-306462 A | 10/2002 |
| JP | 2003-532474 A | 11/2003 |
| JP | 2004-105729 A | 4/2004 |
| TW | 2006-02005 A | 1/2006 |
| WO | WO-01/85010 A2 | 11/2001 |
| WO | WO-2004/041089 A2 | 5/2004 |
| WO | WO-2004/041089 A3 | 5/2004 |
| WO | WO-2006/030406 A2 | 3/2006 |
| WO | WO-2006/030406 A3 | 3/2006 |

OTHER PUBLICATIONS

Rosen, Eric L. et al., "Detection of Primary Breast Carcinoma with a Dedicated, Large-Field-of-View FDG PET Mammography Device: Initial Experience", Radiology, Feb. 2005, vol. 234, No. 2, pp. 527-534.

Supplementary European Search Report for the Application No. EP 07 73 9164 dated Feb. 1, 2010.

Taiwan Office Action for the Application No. 96111145 from Taiwan Patent Office mailed Jan. 16, 2009.

International Search Report for the Application No. PCT/JP2007/055721 mailed Jun. 26, 2007.

Later publication of revised version of International Search Report for the Application No. PCT/JP2007/055721 published Mar. 27, 2008.

* cited by examiner (b)

(a)

MAMMOGRAPHIC APPARATUS

TECHNICAL FIELD

This invention relates to mammographic apparatus for acquiring images of patients' breast areas, and more particularly to a technique for suppressing motions of the breast areas accompanying respiration during radiography.

BACKGROUND ART

Conventionally, in the case of a mammographic apparatus of the X-ray radiographic type for a breast cancer checkup used in a medical institution such as a hospital, whether there is breast cancer is checked by acquiring X-ray photo images, such as transmission X-ray photos or X-ray transmission images, which provide anatomical information on patients' breast areas. Only by checking X-ray photo images, a sufficient breast cancer checkup cannot necessarily be carried out (see Nonpatent Document 1).

Then, it has been proposed to perform a breast cancer checkup by using the PET (positron emission tomography) technique which can provide RI distribution images reflecting a body distribution of a radioisotope introduced into a patient, and photographing RI distribution images of the patient's breast area (see Nonpatent Document 2). Unlike X-ray transmission images which provide anatomical information, RI distribution images provide biofunctional information, and may therefore enable detection of breast cancer overlooked by means of X-ray transmission images.

An apparatus of the PET type, as shown in FIG. 13, includes a top board 91 for supporting a patient M lying on her back or on her side, and a gantry 92 having an opening (tunnel) 92A formed centrally thereof for allowing the top board 91 with the patient M placed thereon to move in and out. A large-sized gantry 92, as shown in FIG. 14, has a ring type gamma-ray detector 93 arranged therein. When RI distribution images are acquired with the conventional apparatus, the gamma-ray detector 93 detects gamma rays (annihilation gamma-rays) of 511 keV energy generated by an RI having reached the breast area Ma after being introduced into the patient M placed on the top board 91 and having entered the opening 92A of gantry 92. On the other hand, at stages downstream of the gamma-ray detector 93, emission data for RI distribution image acquisition are collected according to gamma ray detection signals outputted from the gamma-ray detector 93, and reconstruction processing is carried out based on the emission data collected, to acquire RI distribution images of the breast area Ma of the patient M.

[Nonpatent Document 1]
Radiology 2005; 234: 527-534.
[Nonpatent Document 2]
Nuclear Instrument and Methods in Physics Research A 527 (2004) 82-91

DISCLOSURE OF THE INVENTION

Problem to be Solved by the Invention

However, the apparatus of the X-ray radiographic type and the apparatus of the PET type both have a problem that the breast area Ma moves with respiration of the patient M.

Particularly in the case of X-ray photo images taken instantaneously, as shown in FIG. 15, the breast area Ma of the patient M is strongly pinched with fixing pieces 90 in order to stop movement of the breast area Ma reliably during radiography. Thus, the patient M is subjected to a considerable bodily pain and mental strain.

In the case of the apparatus of the PET type where RI distribution images are acquired from a patient in a sleeping position such as being on her back or side on the top board 91, the apparatus needs a large and spacious installation area. It is therefore unsuitable for a general checkup of breast cancer for numerous, wide-ranging patients, and its spread is difficult.

This invention has been made having regard to the state of the art noted above, and its object is to provide mammographic apparatus not requiring a large installation area in addition to being capable of suppressing motion of a breast area accompanying patient's respiration in a comfortable way.

Means for Solving the Problem

To fulfill the above object, this invention provides the following construction.

A mammographic apparatus for imaging a patient's breast area, according to this invention comprises (A) a seating device for seating the patient; (B) an upper body support device for supporting an upper body of the patient seated on the seating device; and (C) an image pickup device for picking up images of the breast area of the patient seated on the seating device and having the upper body supported by the upper body support device.

When images of the patient's breast area are photographed with the mammographic apparatus of this invention, the patient is seated on the seating device, and the patient's upper body is supported by the upper body support device. Subsequently, images of the patient's breast area are acquired as imaging of the patient's breast area is carried out by the image pickup device.

That is, with the mammographic apparatus of this invention, since the patient's upper body is supported by the upper body support device during radiography for images, the motion of the patient's breast area accompanying the patient's respiration is suppressed easily. Since radiography for images is carried out with the patient in a seated position seated on the seating device, the apparatus is compact and can installed in a limited area, compared with an apparatus that carries out radiography for images with a patient in a sleeping position lying on her back or on a side on a top board. Therefore, according to the mammographic apparatus of this invention, a large installation space is unnecessary in addition to being capable of suppressing the motion of the breast area accompanying the patient's respiration easily.

Preferably, the mammographic apparatus according to this invention further comprises (D) an equipment holding device for holding the upper body support device and the image pickup device; and (E) a raising and lowering device for raising and lowering the equipment holding device together with the upper body support device and the image pickup device, forward and backward relative to the patient.

In this case, after the patient is seated on the seating device and the patient's upper body is supported by the upper body support device, the raising and lowering device is operated to raise or lower the equipment holding device together with the upper body support device and the image pickup device, forward and backward relative to the patient, to set the upper body support device and image pickup device together with the patient to a position suited to the patient's physique and photographing posture. Subsequently, images of the patient's breast area are acquired as imaging of the patient's breast area is carried out by the image pickup device.

The upper body support device is a sternal plate contact device contactable by peripheral portions of the breast area of the patient's sternal plate.

Where the upper body support device is a sternal plate contact device, peripheral portions of the breast area of the patient's sternal plate are placed in contact with the sternal plate contact device. Since the body motion accompanying respiration of the patient shifts from the breast side to the back side, the motion of the breast area of the patient accompanying respiration of the patient is suppressed easily.

Where the upper body support device is a sternal plate contact device, it is preferred that (F) an armrest device is arranged laterally of the sternal plate contact device for receiving right and left arms of the patient.

In this case, the patient having the sternal plate placed in contact with the sternal plate contact device places the right and left arms on the armrest device arranged laterally of the sternal plate contact device. Thus, the patient can comfortably continue to be in the position having the sternal plate placed in contact with the sternal plate contact device.

Preferably, the invention comprising the equipment holding device further comprises (G) a lower leg contact device held by the equipment holding device to be contactable by lower legs of the patient seated on the seating device.

In this case, the patient seated on the seating device has the lower legs contacted by the lower leg contact device. In addition, the lower leg contact device is held by the equipment holding device, and the lower leg contact device is movable with rising and lowering of the equipment holding device. Therefore, even when the equipment holding device is raised and lowered, the patient's lower legs are constantly maintained in contact with the lower leg contact device. As a result, the patient can continue to be seated on the seating device in a stable posture.

Preferably, the invention comprising the sternal plate contact device, as does the invention comprising the equipment holding device, further comprises (D) an equipment holding device for holding the upper body support device and the image pickup device; and (E) a raising and lowering device for raising and lowering the equipment holding device together with the upper body support device and the image pickup device, forward and backward relative to the patient, the seating device also being held by the equipment holding device, said apparatus further comprising (H) a tilt avoiding device for avoiding tilting of the armrest device by raising and lowering the armrest device in an opposite direction in response to raising and lowering of the equipment holding device.

In this case, since the seating device is also held by the equipment holding device, the seating device is also tilted according to the patient's physique and photographing posture, as the equipment holding device is raised or lowered by the raising and lowering device. In addition, the tilt avoiding device avoids tilting of the armrest device by raising and lowering the armrest device in an opposite direction in response to raising and lowering of the equipment holding device. As a result of the armrest device continuing to maintain a horizontal state, there is no fear of the right and left arms of the patient slipping off the armrest device.

In one example of the mammographic apparatus according to this invention, the image pickup device is a gamma-ray detector for receiving the patient's breast area and carrying out radiation image pickup by detecting gamma rays produced by a radioisotope introduced into the patient and having reached the breast area, and outputting gamma ray detection signals, said apparatus further comprising (I) an emission data collecting device for collecting emission data for RI distribution image acquisition according to the gamma ray detection signals outputted from the gamma-ray detector, and (J) an RI distribution image acquiring device for acquiring RI distribution images which are radiographic images of the patient's breast area based on the emission data collected by the emission data collecting device.

In this case, the gamma-ray detector as the image pickup device having received the patient's breast area carries out radiation image pickup to detect gamma rays produced by the radioisotope introduced into the patient and having reached the breast area, and outputs gamma ray detection signals. The emission data collecting device collects emission data for RI distribution image acquisition according to the gamma ray detection signals outputted from the gamma-ray detector. The RI distribution image acquiring device acquires RI distribution images which are radiographic images of the patient's breast area based on the emission data collected by the emission data collecting device.

In the mammographic apparatus for carrying out radiation image pickup, the radioisotope is a positron type radioisotope, the emission data collecting device collecting the emission data according to the gamma ray detection signals when annihilation gamma rays moving in opposite directions are simultaneously detected by the gamma-ray detector.

In this case, the emission data collecting device collects emission data only according to the gamma ray detection signals generated when the gamma-ray detecting device simultaneously detects annihilation gamma-rays generated and traveling in opposite directions in response to annihilation of positrons released from the radioisotope introduced into the patient. It is thus possible to photograph RI distribution images regarding the positron type radioisotope introduced into the patient.

Another example of the mammographic apparatus according to this invention further comprises (K) a light source for emitting light to the patient's breast area, wherein the image pickup device is a light detector for carrying out optical image pickup by detecting absorption light or fluorescence from the patient's breast area irradiated by the light source, and outputting photodetection signals, said apparatus further comprising (L) a light distribution image acquiring device for acquiring light distribution images which are optical images of the patient's breast area according to the photodetection signals outputted from the light detector.

In this case, the light detector as the image pickup device carries out optical image pickup to detect absorption light or fluorescence from the patient's breast area irradiated by the light source, and output photodetection signals. The light distribution image acquiring device acquires light distribution images which are optical images of the patient's breast area according to the photodetection signals outputted from the light detector.

In the mammographic apparatus according to this invention, the image pickup device is applicable to the type that receives both of breasts, and picks up images thereof simultaneously, and the image pickup device is applicable also to the type that receives one breast separately, and picks up images of right and left breasts individually.

Apart from such mammographic apparatus having the seating device, a mammographic apparatus without the seating device is also possible.

Thus, a mammographic apparatus for imaging a patient's breast area, according to this invention, comprises (b) an upper body support device for supporting an upper body of a patient in a standing or seated position; and (c) an image pickup device for picking up images of the breast area of the patient in the standing or seated position and having the upper body supported by the upper body support device.

When images of the patient's breast area are photographed with the mammographic apparatus of this invention, the upper body support device supports the upper body of the patient in a standing or seated position. Subsequently, images of the patient's breast area are acquired as imaging of the patient's breast area is carried out by the image pickup device.

That is, with the mammographic apparatus of this invention, as with the mammographic apparatus having the seating device, since the patient's upper body is supported by the upper body support device during radiography for images, the motion of the patient's breast area accompanying the patient's respiration is suppressed easily. Since radiography for images is carried out with the patient in a standing or seated position, the apparatus is compact and can installed in a limited area, compared with an apparatus that carries out radiography for images with a patient in a sleeping position lying on her back or on a side on a top board. Therefore, according to the mammographic apparatus of this invention, a large installation space is unnecessary in addition to being capable of suppressing the motion of the breast area accompanying the patient's respiration easily.

Preferably, the mammographic apparatus according to this invention further comprises (d) a height adjusting device for holding the upper body support device and the image pickup device and adjusting a height thereof, or for vertically moving the patient to adjust a relative height between the upper body support device and the image pickup device, and the patient.

In this case, the height adjusting device holding the upper body support device and image pickup device, adjusts their height to the patient's height and photographing posture, with the upper body support device supporting the upper body of the patient and the image pickup device picking up images of the breasts. Alternatively, the height adjusting device moves the patient vertically to adjust the relative height between the upper body support device and image pickup device, and the patient. The upper body support device supports the upper body of the patient, and the image pickup device picks up images of the breasts. As a result, height adjustment can be carried out according to height differences and photographing postures, to enable an image pick-up suited to the height and photographing posture of each patient.

In the mammographic apparatus without the seating device, as in the mammographic apparatus having the seating device, the upper body support device is a sternal plate contact device contactable by peripheral portions of the breast area of the patient's sternal plate.

Where the upper body support device is a sternal plate contact device, peripheral portions of the breast area of the patient's sternal plate are placed in contact with the sternal plate contact device. Since the body motion accompanying respiration of the patient shifts from the breast side to the back side, the motion of the breast area of the patient accompanying respiration of the patient is suppressed easily.

In the mammographic apparatus without the seating device, as in the mammographic apparatus having the seating device, where the upper body support device is a sternal plate contact device, it is preferred that (f) an armrest device is arranged laterally of the sternal plate contact device for receiving right and left arms of the patient.

In this case, the patient having the sternal plate placed in contact with the sternal plate contact device places the right and left arms on the armrest device arranged laterally of the sternal plate contact device. Thus, the patient can comfortably continue to be in the position having the sternal plate placed in contact with the sternal plate contact device.

As in the mammographic apparatus having the seating device, in one example of the mammographic apparatus without the seating device, the image pickup device is a gamma-ray detector for receiving the patient's breast area and carrying out radiation image pickup by detecting gamma rays produced by a radioisotope introduced into the patient and having reached the breast area, and outputting gamma ray detection signals, said apparatus further comprising (i) an emission data collecting device for collecting emission data for RI distribution image acquisition according to the gamma ray detection signals outputted from the gamma-ray detector, and (j) an RI distribution image acquiring device for acquiring RI distribution images which are radiographic images of the patient's breast area based on the emission data collected by the emission data collecting device.

In this case, the gamma-ray detector as the image pickup device having received the patient's breast area carries out radiation image pickup to detect gamma rays produced by the radioisotope introduced into the patient and having reached the breast area, and outputs gamma ray detection signals. The emission data collecting device collects emission data for RI distribution image acquisition according to the gamma ray detection signals outputted from the gamma-ray detector. The RI distribution image acquiring device acquires RI distribution images which are radiographic images of the patient's breast area based on the emission data collected by the emission data collecting device.

As in the mammographic apparatus having the seating device, in the mammographic apparatus without the seating device, and in the mammographic apparatus for carrying out radiation image pickup, the radioisotope is a positron type radioisotope, the emission data collecting device collecting the emission data according to the gamma ray detection signals when annihilation gamma rays moving in opposite directions are simultaneously detected by the gamma-ray detector.

In this case, the emission data collecting device collects emission data only according to the gamma ray detection signals generated when the gamma-ray detecting device simultaneously detects annihilation gamma-rays generated and traveling in opposite directions in response to annihilation of positrons released from the radioisotope introduced into the patient. It is thus possible to photograph RI distribution images regarding the positron type radioisotope introduced into the patient.

As does the mammographic apparatus having the seating device, another example of the mammographic apparatus without the seating device further comprises (k) a light source for emitting light to the patient's breast area, wherein the image pickup device is a light detector for carrying out optical image pickup by detecting absorption light or fluorescence from the patient's breast area irradiated by the light source, and outputting photodetection signals, said apparatus further comprising (l) a light distribution image acquiring device for acquiring light distribution images which are optical images of the patient's breast area according to the photodetection signals outputted from the light detector.

In this case, the light detector as the image pickup device carries out optical image pickup to detect absorption light or fluorescence from the patient's breast area irradiated by the light source, and output photodetection signals. The light distribution image acquiring device acquires light distribution images which are optical images of the patient's breast area according to the photodetection signals outputted from the light detector.

As in the mammographic apparatus having the seating device, in the mammographic apparatus without the seating device, the image pickup device is applicable to the type that receives both of breasts, and picks up images thereof simultaneously, and the image pickup device is applicable also to the type that receives one breast separately, and picks up images of right and left breasts individually.

Effects of the Invention

With the mammographic apparatus of this invention, since the patient's upper body is supported by the upper body support device during radiography for images, the motion of the patient's breast area accompanying the patient's respiration is suppressed. Since radiography for images is carried out with the patient in a seated position seated on the seating device, or with the patient in a standing or seated position, the apparatus is compact and can installed in a limited area, compared with an apparatus that carries out radiography for images with a patient in a sleeping position lying on her back or on a side on a top board.

Therefore, according to the mammographic apparatus of this invention, a large installation space is unnecessary in addition to being capable of suppressing the motion of the breast area accompanying the patient's respiration.

DESCRIPTION OF REFERENCES 1, 17, 31 . . . examining table
2 . . . seating unit (seating device)
3 . . . sternal plate contact box (upper body support device, sternal plate contact device)
4 . . . gamma-ray detector (image pickup device)
5 . . . equipment holding arm (equipment holding device)
6, 19 . . . raising and lowering mechanism (raising and lowering device)
7 . . . armrest boards (armrest device)
9 . . . lower leg contact part (lower leg contact device)
12 . . . emission data collecting unit (emission data collecting device)
13 . . . RI distribution image acquiring unit (RI distribution image acquiring device)
18 . . . board tilt avoiding mechanism (tilt avoiding device)
32, 33 . . . height adjusting mechanism (height adjusting device)
41 . . . light source
42 . . . light detector (image pickup device)
43 . . . light distribution image acquiring unit (light distribution image acquiring device)
M . . . patient
Ma . . . breast area Embodiment 1

Figure 1:
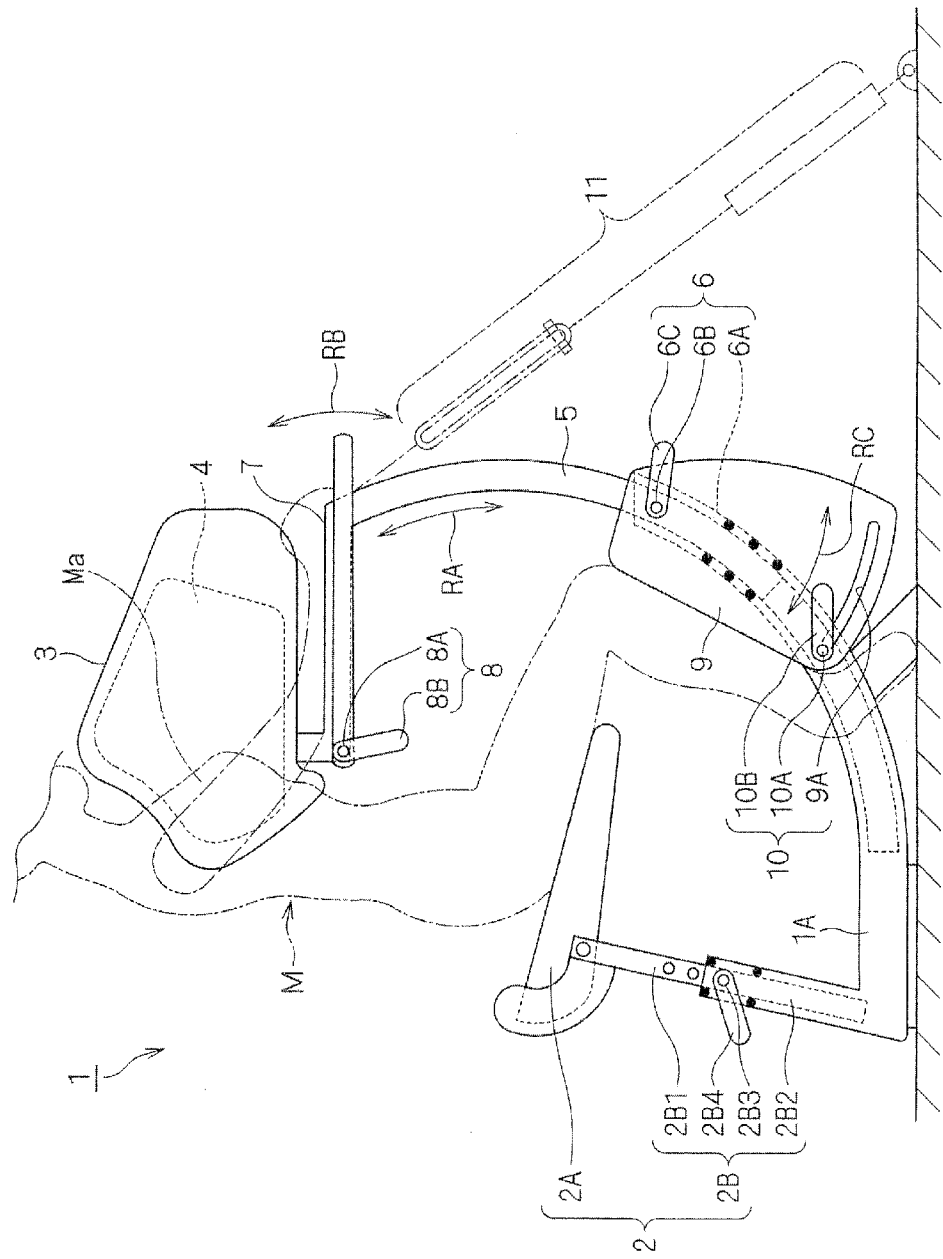
FIG. 1 is an elevational view showing a non-tilting state of an examining table of a mammographic apparatus in Embodiment 1.
Figure 2:
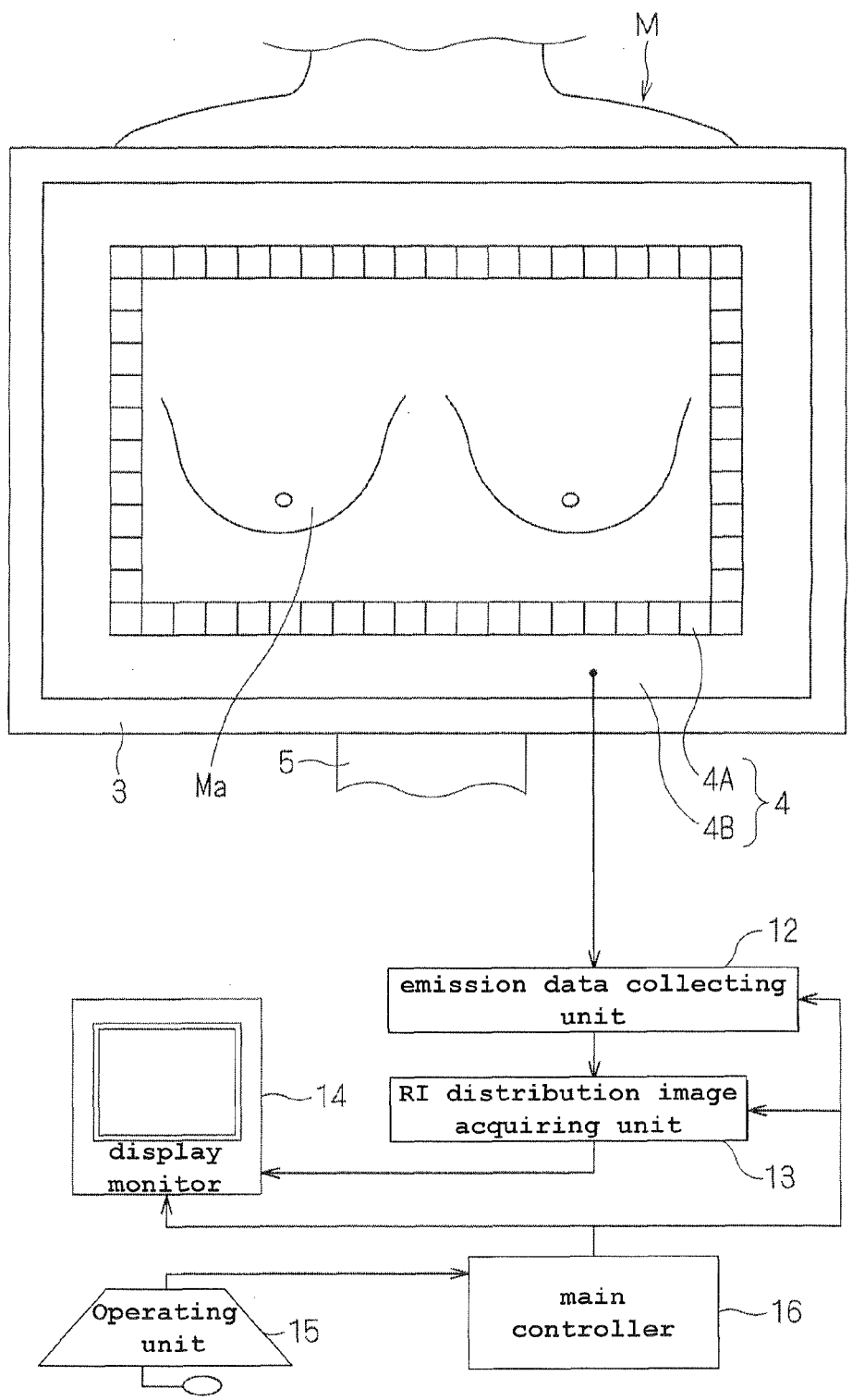
FIG. 2 is a block diagram showing a principal portion of the mammographic apparatus in Embodiment 1.

Embodiment 1 of a mammographic apparatus of this invention will be described with reference to the drawings. FIG. 1 is an elevational view showing an examining table of a mammographic apparatus of the PET (positron emission tomography) type in Embodiment 1. FIG. 2 is a block diagram showing a principal portion of the mammographic apparatus in Embodiment 1.

As shown in FIG. 1, the mammographic apparatus in Embodiment 1 includes a seating unit 2 for seating a patient M who is the subject of examination at an examining table 1. The seating unit 2 includes a seat 2A on which the patient M puts her buttocks, and a height adjusting mechanism 2B for adjusting height of the seat 2A. The seating unit 2 corresponds to the seating device in this invention.

The height adjusting mechanism 2B has a seat support rod 2B1 with the seat 2A attached to the upper end thereof, and a pipe 2B2 erected on an examining table base 1A. The seat support rod 2B1 has a lower portion thereof inserted into the pipe 2B2. In addition, a fixing screw 2B3 is provided having a forward end thereof extending through the pip 2B2 to fix the seat support rod 2B1 to the pipe 2B2, and a control lever 2B4 provided for turning this fixing screw 2B3.

When adjusting the height of the seat 2A, the control lever 2B4 is first operated to turn the fixing screw 2B3 in a loosening direction. Then, the forward end of the fixing screw 2B3 will separate from the seat support rod 2B1 to cancel a fixed state of the seat support rod 2B1. The seat support rod 2B1 is slid upward or downward together with the seat 2A. After appropriately sliding the seat support rod 2B1 to set the seat 2A to a desired height, the control lever 2B4 is operated to turn the fixing screw 2B3 in a tightening direction. Then, the forward end of the fixing screw 2B3 will be pressed on the seat support rod 2B1 to combine the seat support rod 2B1 with the pipe 2B2, placing the seat support rod 2B1 in the fixed state again. This results in the seat 2A having been changed to the desired height.

The examining table 1 of the apparatus in Embodiment 1 includes a sternal plate contact box 3 for contact with peripheral portions of a breast area Ma of the patient M seated on the seating unit 2, and a gamma-ray detector 4 for picking up gamma-ray images of the breast area Ma of the patient M seated on the seating unit 2 with the sternal plate contacting the sternal plate contact box 3. The sternal plate contact box 3 is open at the side facing the patient M, and the peripheral portions of the breast area Ma of the patient M contact edges of the opening of the sternal plate contact box 3. The sternal plate contact box 3 corresponds to the upper body support device and the sternal plate contact device in this invention. The gamma-ray detector 4 corresponds to the image pickup device in this invention.

As shown in FIG. 2, the square frame-like gamma-ray detector 4 is housed in an inner space of the sternal plate contact box 3. When the patient M seated on the seating unit 2 places the peripheral portions of the breast area Ma of the sternal plate in contact with the sternal plate contact box 3, the breast area Ma of the patient M is received by the gamma-ray detector 4. Usually, a size is set for the gamma-ray detector 4 to receive a range including the shoulder joints at the lateral ends of the breast area Ma.

The gamma-ray detector 4 includes a scintillator unit 4A for converting gamma rays into light, and a photoelectric conversion device 4B for detecting light released from the scintillator unit 4A and outputting electric signals as gamma-ray detection signals according to incident position and intensity of the light on an optical incidence plane. This gamma-ray detector 4 carries out gamma-ray image pickup by detecting gamma rays generating from a radioisotope (RI) introduced into the patient M reaching the breast area Ma, and outputting the gamma-ray detection signals.

The examining table 1 of the apparatus in Embodiment 1 further includes a substantially arcuate equipment holding arm 5 holding the sternal plate contact box 3 and gamma-ray detector 4, a raising and lowering mechanism 6 for raising and lowering this equipment holding arm 5 together with the sternal plate contact box 3 and gamma-ray detector 4, and back and forth relative to the patient M, as indicated by arrow RA in FIG. 1. The equipment holding arm 5 has an upper end portion bent to extend straight inward to define a linear region. The sternal plate contact box 3 and gamma-ray detector 4 are mounted on and held by this linear region. The equipment holding arm 5 corresponds to the equipment holding device in this invention. The raising and lowering mechanism 6 corresponds to the raising and lowering device in this invention.

Specifically, the raising and lowering mechanism 6 has an arcuate long tube 6A fixed to the examining table base 1A. The equipment holding arm 5 has a lower end portion inserted in the long cylinder 6A to be movable in and out. In addition, a fixing screw 6B is provided having a forward end thereof extending through the long tube 6A to fix the equipment holding arm 5 to the long tube 6A, and a control lever 6C provided for turning this fixing screw 6B.

When raising and lowering the equipment holding arm 5 with the raising and lowering mechanism 6, the control lever 6C is first operated to turn the fixing screw 6B in a loosening direction. Then, the forward end of the fixing screw 6B will separate from the equipment holding arm 5 to cancel a fixed state of the equipment holding arm 5. The equipment holding arm 5 is slid longitudinally of the arm together with the sternal plate contact box 3 and gamma-ray detector 4. After appropriately sliding the equipment holding arm 5 to set it to a desired raise/lower state, the control lever 6C is operated to turn the fixing screw 6B in a tightening direction. Then, the forward end of the fixing screw 6B will be pressed on the equipment holding arm 5 to combine the equipment holding arm 5 with the long tube 6A, placing the equipment holding arm 5 in the fixed state again. This results in the equipment holding arm 5 having been changed to the desired raise/lower state.

Figure 3:
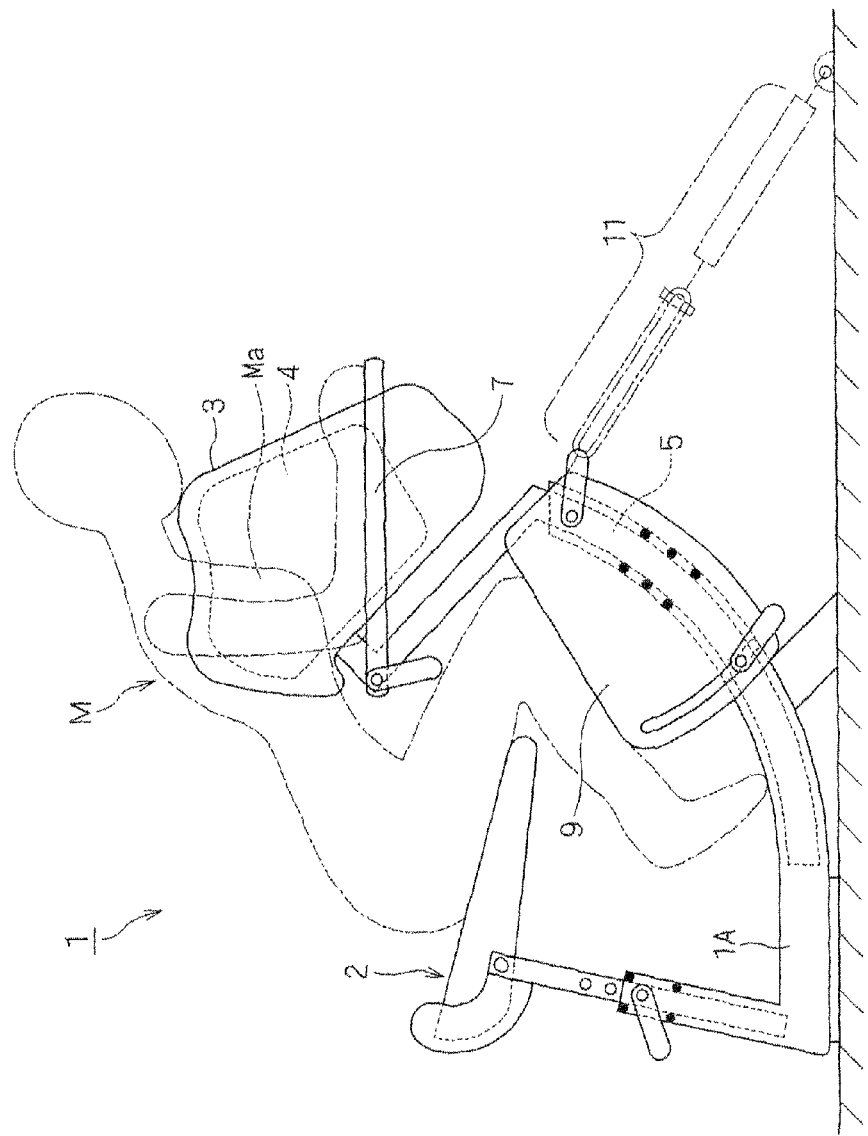
FIG. 3 is an elevational view showing a maximum tilting state of the examining table of the mammographic apparatus in Embodiment 1.

When the equipment holding arm 5 is tilted deep by the raising and lowering mechanism 6, as shown in FIG. 3, the patient M seated on the seating unit 2 will be in a deep forward-leaning state. When the patient M is in the deep forward-leaning state, the peripheral portions of the breast area Ma of the sternal plate are in contact with the sternal plate contact box 3 almost over the entire circumference, to be firmly supported.

The examining table 1 of the apparatus in Embodiment 1 includes armrest boards 7 arranged at sides of the sternal plate contact box 3 for the patient M to put the right and left arms. Although FIG. 1 shows only the armrest board 7 for receiving the right arm, the armrest board 7 for receiving the left arm also is provided at the opposite side. The patient M places the right and left arms on the armrest boards 7, whereby the patient M can comfortably continue the position for keeping the sternal plate in contact with the sternal plate contact box 3. The armrest boards 7 correspond to the armrest device in this invention.

Further, a board inclination adjusting mechanism 8 is provided for adjusting inclination of the armrest boards 7. The board inclination adjusting mechanism 8 includes a fixing screw 8A extending horizontally through a proximal end of the armrest board 7 for tightening and fixing the armrest board 7 to the equipment holding arm 5, and a control lever 8B for turning this fixing screw 8A.

When adjusting the inclination of the armrest board 7, the control lever 8B is first operated to turn the fixing screw 8A in a loosening direction. Then, a fixed state of the armrest board 7 is canceled. The armrest board 7 is now rotatable about the central axis of the fixing screw 8A, as indicated by arrow RB in FIG. 1, to change its inclination. Then, the armrest board 7 is turned to a desired inclination, and the control lever 8B is operated to turn the fixing screw 8A in a tightening direction. Then, the armrest board 7 will return to the fixed state again. This results in the armrest board 7 having been changed to the desired inclination.

In addition, the examining table 1 of the apparatus in Embodiment 1 includes a lower leg contact part 9 held by the equipment holding arm 5 for contacting the lower legs of patient M seated on the seating unit 2. A part inclination adjusting mechanism 10 is provided for adjusting the inclination of the lower leg contact part 9.

The part inclination adjusting mechanism 10 includes a slot 9A extending along a lower side adjacent the lower end of the lower leg contact part 9, a fixing screw 10A inserted in the slot 9A for tightening and fixing the lower leg contact part 9 to the equipment holding arm 5, and a control lever 10B for turning the fixing screw 10A.

When adjusting the inclination of the lower leg contact part 9, the control lever 10B is first operated to turn the fixing screw 10A in a loosening direction. Then, a fixed state of the lower leg contact part 9 is canceled. The lower leg contact part 9 is now rockable about the fixing screw 6B, as indicated by arrow RC in FIG. 1, to change its inclination. Then, the lower leg contact part 9 is moved to a desired inclination, and the control lever 10B is operated to turn the fixing screw 10A in a tightening direction. Then, the lower leg contact part 9 will return to the fixed state again, This results in the lower leg contact part 9 having been changed to the inclination.

Further, as shown in an alternate long and short dash line in FIG. 1, the examining table 1 of the apparatus in Embodiment 1 may have a shock relaxing mechanism 11 of the air damper attached thereto. The shock relaxing mechanism 11 may absorb a shock produced when the sternal plate of the patient M contacts the sternal plate contact box 3 or when the equipment holding arm 5 is raised or lowered, to protect the patient M from damage by the shock.

On the other hand, as shown in FIG. 2, the mammographic apparatus in Embodiment 1 includes, arranged downstream of the gamma-ray detector 4, an emission data collecting unit 12 for collecting emission data for RI distribution image acquisition according to the gamma ray detection signals outputted from the gamma-ray detector 4, an RI distribution image acquiring unit 13 for acquiring RI distribution images of the breast area Ma of patient M based on the emission data collected by the emission data collection unit 12. In addition, a display monitor 14 is provided for displaying the RI distribution images, operating menus of the apparatus and so on, and an operating unit 15 is provided for inputting data, commands and the like required for operation of the apparatus. The emission data collecting unit 12 corresponds to the emission data collecting device in this invention. The RI distribution image acquiring unit 13 corresponds to the RI distribution image acquiring device in this invention.

The emission data collecting unit 12 collects emission data for RI distribution image acquisition according to the gamma ray detection signals outputted from gamma-ray detector 4. In addition, the emission data collecting unit 12 collects emission data only according to gamma ray detection signals generated when the gamma-ray detector 4 simultaneously detects annihilation gamma-rays generated and traveling in opposite directions in response to annihilation of positrons released from the radioisotope. That is, the apparatus in Embodiment 1 is a mammographic apparatus of the PET type. The positron type RI introduced into the patient M may be 11C, 13N, 15O or 18F.

The RI distribution image acquiring unit 13 carries out reconstruction processing based on the emission data collected by the emission data collecting unit 12, to acquire tomogram type or planar image type RI distribution images of the breast area Ma of patient M. The display monitor 14 displays on the screen the RI distribution images acquired by the RI distribution image acquiring unit 13.

A main controller 16 is constructed of a computer and its operating program as central components thereof, and plays a role of operating the apparatus normally by outputting commands and data to each part in response to instructions inputted from operating unit 15 and progress of radiography.

When RI distribution images of the breast area Ma of patient M are photographed with the mammographic apparatus in Embodiment 1, the examining table 1 usually is adjusted, before the patient M sits on the seating unit 2, to set the sternal plate contact box 3 and gamma-ray detector 4 to a position suited to the physique and photographing posture of the patient M by operating the raising and lowering mechanism 6 to raise or lower, and forward or backward relative to the patient M, the equipment holding arm 5 holding the sternal plate contact box 3 and gamma-ray detector 4, together with the sternal plate contact box 3 and gamma-ray detector 4. The armrest boards 7 and lower leg contact part 9 are also adjusted, as necessary, according to the physique and photographing posture of the patient M.

Figure 4:
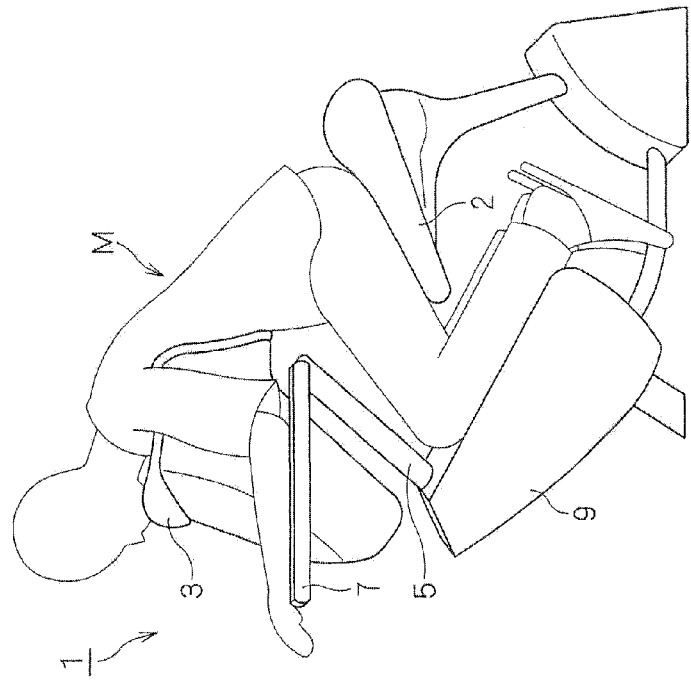
FIG. 4 presents views showing situations at times of radiography by the apparatus in Embodiment 1, in which (a) is a perspective view showing a state where a patient is made to sit straight, and (b) is a perspective view showing a state where the patient is made to sit leaning forward.
Figure 4:
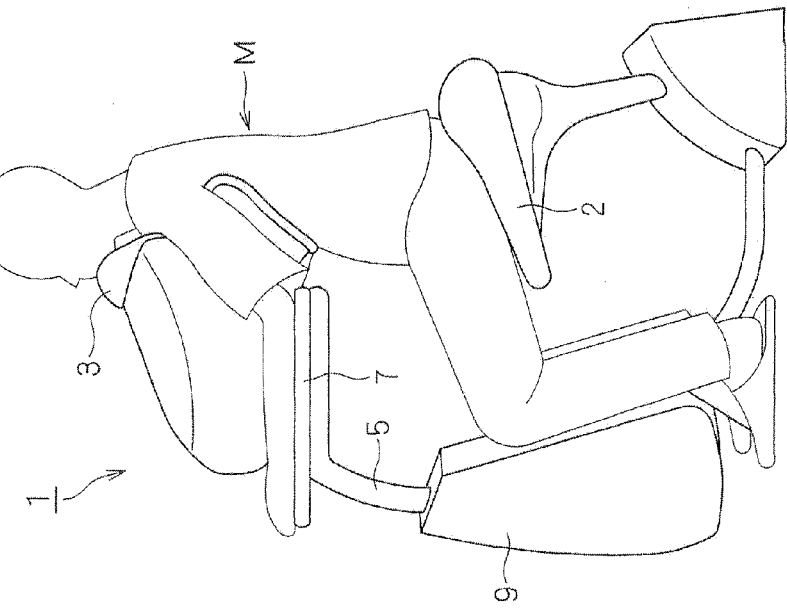

The photographing posture may be such that, as shown in FIGS. 1 and 4 (a), the patient M sits straight up to be photographed or, as shown in FIGS. 3 and 4 (b), the patient M sits leaning forward to be photographed. Therefore, the position, etc. of the sternal plate contact box 3 and gamma-ray detector 4 is adjusted beforehand. The inclination of the armrest boards 7 is usually adjusted to be horizontal for any photographing posture.

Subsequently, the patient M is asked to sit on the seating unit 2 and place the peripheral portions of the breast area Ma of the sternal plate in contact with the sternal plate contact box 3.

Alternatively, in the case of the apparatus in Embodiment 1, it is also possible to adjust the position of the sternal plate contact box 3 and gamma-ray detector 4 after the patient M sits on the seating unit 2 with the peripheral portions of the breast area Ma of the sternal plate placed in contact with the sternal plate contact box 3.

Then, RI distribution images of the breast area Ma of the patient M are acquired as the gamma-ray detector 4 carries out gamma-ray image pickup of the breast area Ma of the patient M seated on the seating unit 2 with the peripheral portions of the breast area Ma of the sternal plate placed in contact with the sternal plate contact box 3.

In the case of the apparatus in Embodiment 1 having the construction described above, the peripheral portions of the breast area Ma of the sternal plate of patient M is in contact with the sternal plate contact box 3 during radiography for RI distribution images. Since the body motion accompanying respiration of the patient M shifts from the breast side to the back side, the motion of the breast area Ma of the patient M accompanying respiration of the patient M is suppressed easily. When the patient M is in a deep forward-leaning state, as shown in FIGS. 3 and 4 (b), the peripheral portions of the breast area Ma of the sternal plate of patient M is in contact with the sternal plate contact box 3 almost over the entire circumference. Therefore, the motion of the breast area Ma of the patient M accompanying respiration of the patient M is suppressed reliably.

In addition, in the case of the apparatus in Embodiment 1, since radiography for RI distribution images is carried out with the patient M in a seated position seated on the seating unit 2, the apparatus is compact and therefore may be installed in a limited area, compared with an apparatus which carries out radiography for RI distribution images with a patient in a sleeping position lying on the back or on a side on the top board.

Therefore, according to the mammographic apparatus in Embodiment 1, a large installation space is unnecessary in addition to being capable of easily suppressing the motion of the breast area Ma accompanying respiration of the patient M.

In the case of the apparatus in Embodiment 1, in addition to the patient M seated on the seating unit 2 having the lower legs contacted by the lower leg contact part 9, the lower leg contact part 9 is held by the equipment holding arm 5, and the lower leg contact part 9 moves with raising and lowering of the equipment holding arm 5. Even if the equipment holding arm 5 is raised or lowered, the state of the lower legs of the patient M being contacted by the lower leg contact part 9 is maintained constantly. As a result, the patient M can remain seated in a stable position on the seating unit 2.

Embodiment 2

Figure 5:
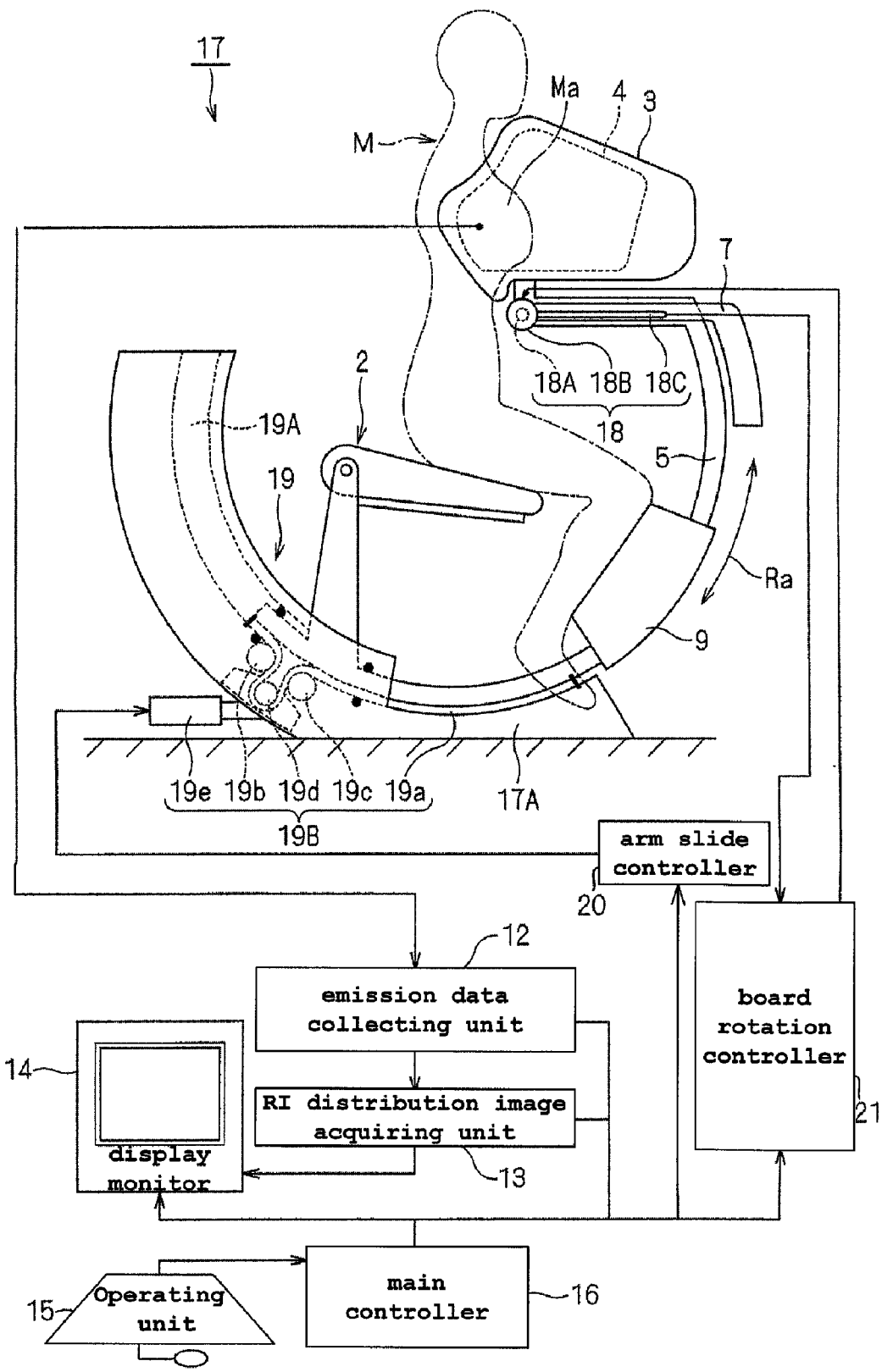
FIG. 5 is a block diagram showing an overall construction of a mammographic apparatus in Embodiment 2.

Embodiment 2 of a mammographic apparatus of this invention will be described with reference to the drawings. FIG. 5 is a block diagram showing an overall construction of a mammographic apparatus of the PET type in Embodiment 2.

In the mammographic apparatus in Embodiment 2, as shown in FIG. 5, an examining table 17 has also a seating unit 2 held by an equipment holding arm 5, and a board tilt avoiding mechanism 18 for avoiding tilting of armrest boards 7 by raising or lowering the armrest boards in an opposite direction to raising or lowering of the equipment holding arm 5, thereby to maintain the armrest boards 7 in a horizontal state at all times. Besides, the raising and lowering of the equipment holding arm 5 are carried out by power drive such as by electric power. The other aspects are substantially the same as in Embodiment 1. Only different points will be described, and description of the common points will be omitted. The board tilt avoiding mechanism 18 corresponds to the board tilt avoiding device in this invention.

In the mammographic apparatus in Embodiment 2, a raising and lowering mechanism 19 for raising and lowering the equipment holding arm 5 together with the sternal plate contact box 3 and gamma-ray detector 4, and back and forth relative to the patient M, as indicated by arrow Ra in FIG. 5, has an engaging groove 19A formed in an examining table base 17A, the equipment holding arm 5 being engaged with the engaging groove 19A to be longitudinally slidable, and in addition has an arm slide mechanism 19B for sliding the equipment holding arm 5 longitudinally of the engaging groove 19A. The raising and lowering mechanism 19 corresponds to the raising and lowering device in this invention.

The arm slide mechanism 19B includes a belt 19a having opposite ends thereof fixed to one end and the other end of the equipment holding arm 5, and in addition guide pulleys 19b, 19c and a drive pulley 19d installed on the examining table base 17A, and an electromotive or hydraulic power motor 19e for rotating the drive pulley 19d, the belt 19a being wound around and extending between the guide pulleys 19b, 19c and drive pulley 19d. Therefore, as the belt 19a is transported with rotation of the power motor 19e, the equipment holding arm 5 is pulled by the belt 19a to slide longitudinally of the engaging groove 19A as indicated by arrow Ra, thereby raising or lowering the equipment holding arm 5. The sliding direction of the equipment holding arm 5 is reversed when the direction of rotation of power motor 19e changes. The arm slide mechanism 19B, while receiving slide control data according to operation of the operator from an arm slide controller 20, raises or lowers the equipment holding arm 5 to follow the operation of the operator.

Figure 6:
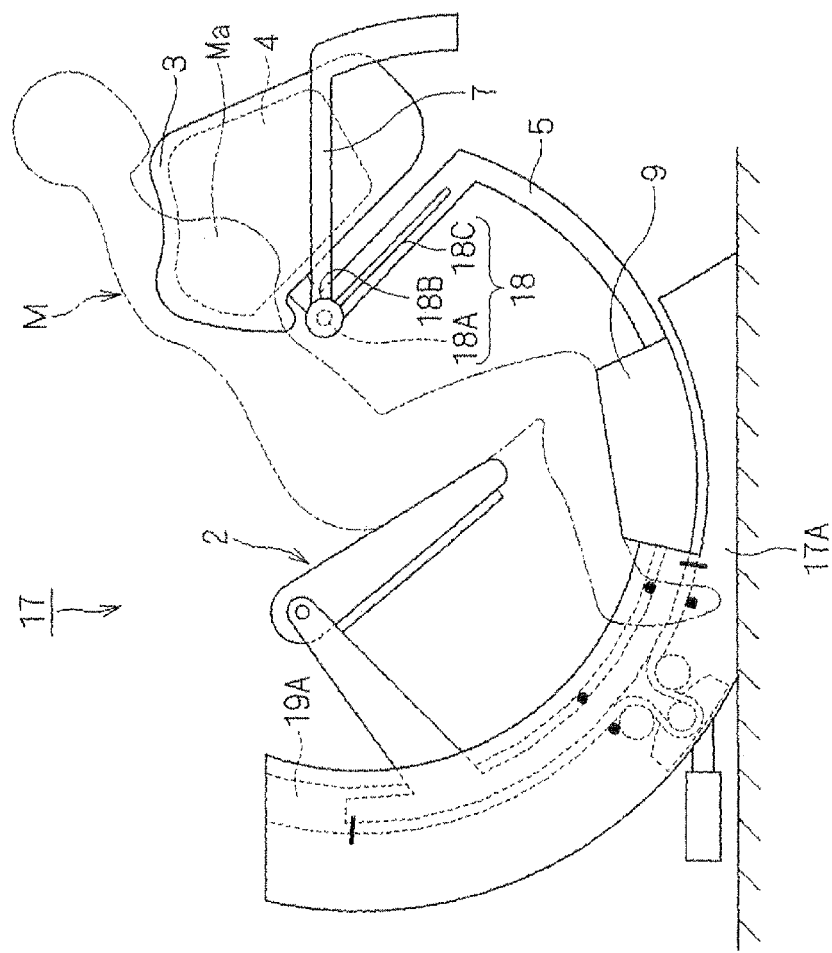
FIG. 6 is an elevational view showing a maximum tilting state of an examining table of the mammographic apparatus in Embodiment 1.

With the apparatus in Embodiment 2, since the seating unit 2 is also held by the equipment holding arm 5, the seating unit 2 is also raised and lowered with the raising and lowering of the equipment holding arm 5. For example, when the equipment holding arm 5 tilts as shown in FIG. 6, the seating unit 2 will also tilt together with the sternal plate contact box 3, gamma-ray detector 4 and lower leg contact part 9.

The board tilt avoiding mechanism 18 includes a support shaft 18A for rotatably supporting the armrest boards 7, an electric motor 18B for rotating the support shaft 18A about the central axis of the support shaft 18A, and a horizon sensor 18C for detecting tilt angles from the horizontal occurring with tilting of the equipment holding arm 5, and outputting angle detection signals. The board tilt avoiding mechanism 18 constantly maintains the armrest boards 7 in a horizontal state, with the electric motor 18B rotating the support shaft 18A in a reverse direction by an angle detected by the horizon sensor 18C. The board tilt avoiding mechanism 18 maintains the armrest boards 7 in a horizontal state while receiving rotation control data from a board rotation controller 21 according to an angle detecting signal outputted from the horizon sensor 18C.

When RI distribution images of the breast area Ma of patient M are photographed with the mammographic apparatus in Embodiment 2, as shown in FIG. 5, the patient M first sits on the seating unit 2, and next the raising and lowering mechanism 19 is operated to tilt the equipment holding arm 5 together with the sternal plate contact box 3 and gamma-ray detector 4 forward or backward relative to the patient M. Thus, as shown in FIG. 6, the sternal plate contact box 3, gamma-ray detector 4 and patient M are set all together to a position suited to the physique and photographing posture of the patient M.

In the case of the apparatus in Embodiment 2, since the seating unit 2 is also held by the equipment holding arm 5, the seating unit 2 is also tilted according to the physique and photographing posture of the patient M, with the raising and lowering of the equipment holding arm 5 caused by the raising and lowering mechanism 19. In addition, tilting of the armrest boards 7 is avoided by the board tilt avoiding mechanism 18 causing a reversed raising or lowering, following a raising or lowering of the equipment holding arm 5, thereby continuously maintaining the armrest boards 7 in a horizontal state. As a result, there is no fear of the right and left arms of the patient M slipping off the armrest boards 7.

Embodiment 3

Embodiment 3 of a mammographic apparatus of this invention will be described with reference to the drawings.

Figure 7:
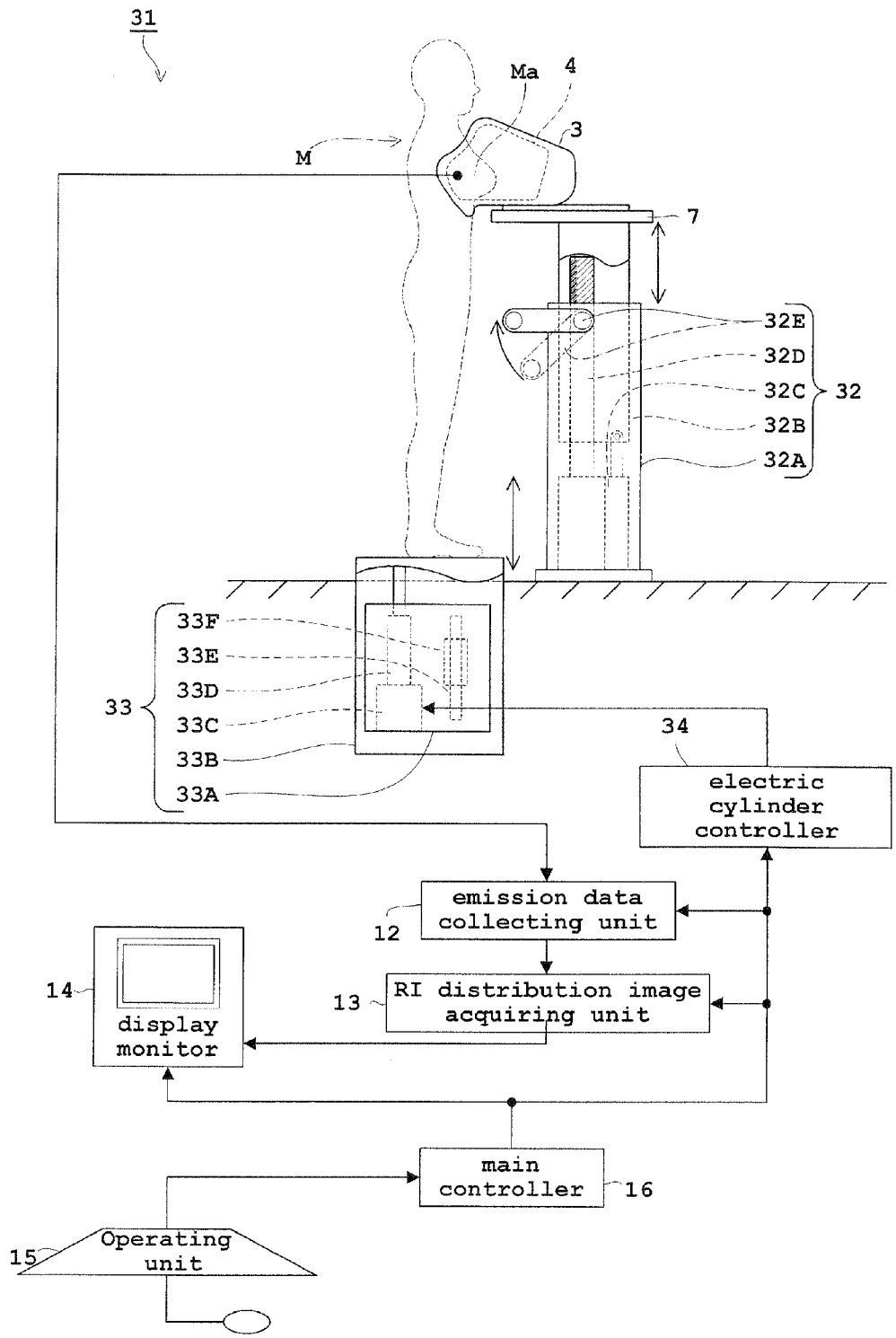
FIG. 7 is a block diagram showing a principal portion of a mammographic apparatus in Embodiment 3.

In the mammographic apparatus in Embodiment 3, as shown in FIG. 7, an examining table 31 does not include a seating unit 2, but include a height adjusting mechanism 32 for holding the sternal plate contact box 3 and gamma-ray detector 4 and adjusting their height, and a height adjusting mechanism 33 of the platform type for moving the patient M up and down to adjust a relative height between the sternal plate contact box 3 and gamma-ray detector 4, and the patient M. The other aspects are substantially the same as in Embodiments 1 and 2. Only different points will be described, and description of the common points will be omitted. The height adjusting mechanisms 32, 33 correspond to the height adjusting device in this invention.

In the apparatus in Embodiment 3, the sternal plate contact box 3 supports the upper body of the patient M in a standing position or a seated position seated on a wheelchair, and the gamma-ray detector 4 picks up images of the breast area Ma of the patient M supported in the standing or seated position by the sternal plate contact box 3.

The height adjusting mechanism 32 includes a fixed base 32A, a movable base 32B vertically movable relative to the fixed base 32A, a gas spring 32C and a ball screw 32D arranged on the fixed base 32A, and a locking lever 32E. One end of the gas spring 32C is connected to the movable base 32B. When the gas spring 32C causes the movable base 32B to move up and down vertically along the ball screw 32D, the movable base 32B can be moved freely and manually without a burden. By tightening the locking lever 32D in a predetermined position to stop rotation of the ball screw 32D, thereby fixing the movable base 32B. The movable base 32B is coupled to the sternal plate contact box 3 and gamma-ray detector 4, and coupled also to the armrest boards 7. Thus, the sternal plate contact box 3, gamma-ray detector 4 and armrest boards 7 are held by the movable base 32B.

The height adjusting mechanism 33 of the platform type includes a fixed base 33A installed under the floor, a movable base 33B vertically movable relative to the fixed base 33A, a motor 33C, a motor cylinder 33D and a guide rail 33E arranged on the fixed base 33A, and a block 33F arranged on the movable base 33B. One end of the motor cylinder 33D is connected to the motor 33C, and the other end remote from the connection to the motor 33C is connected to the movable base 33B. The guide rail 33E is fitted in the block 33F.

When the motor 33C is operated, the drive of the motor 33C expands and contracts the motor cylinder 33D vertically. With the expansion and contraction of the motor cylinder 33D, the block 33F moves up and down vertically along the guide rail 33E, and the movable base 33B having the block 33F and connected to the motor cylinder 33D moves up and down vertically relative to the fixed base 33A. The motor 33C, while receiving height control data according to operation by the operator from a motor cylinder controller 34, vertically moves the movable base 33B to a predetermined height.

Figure 8:
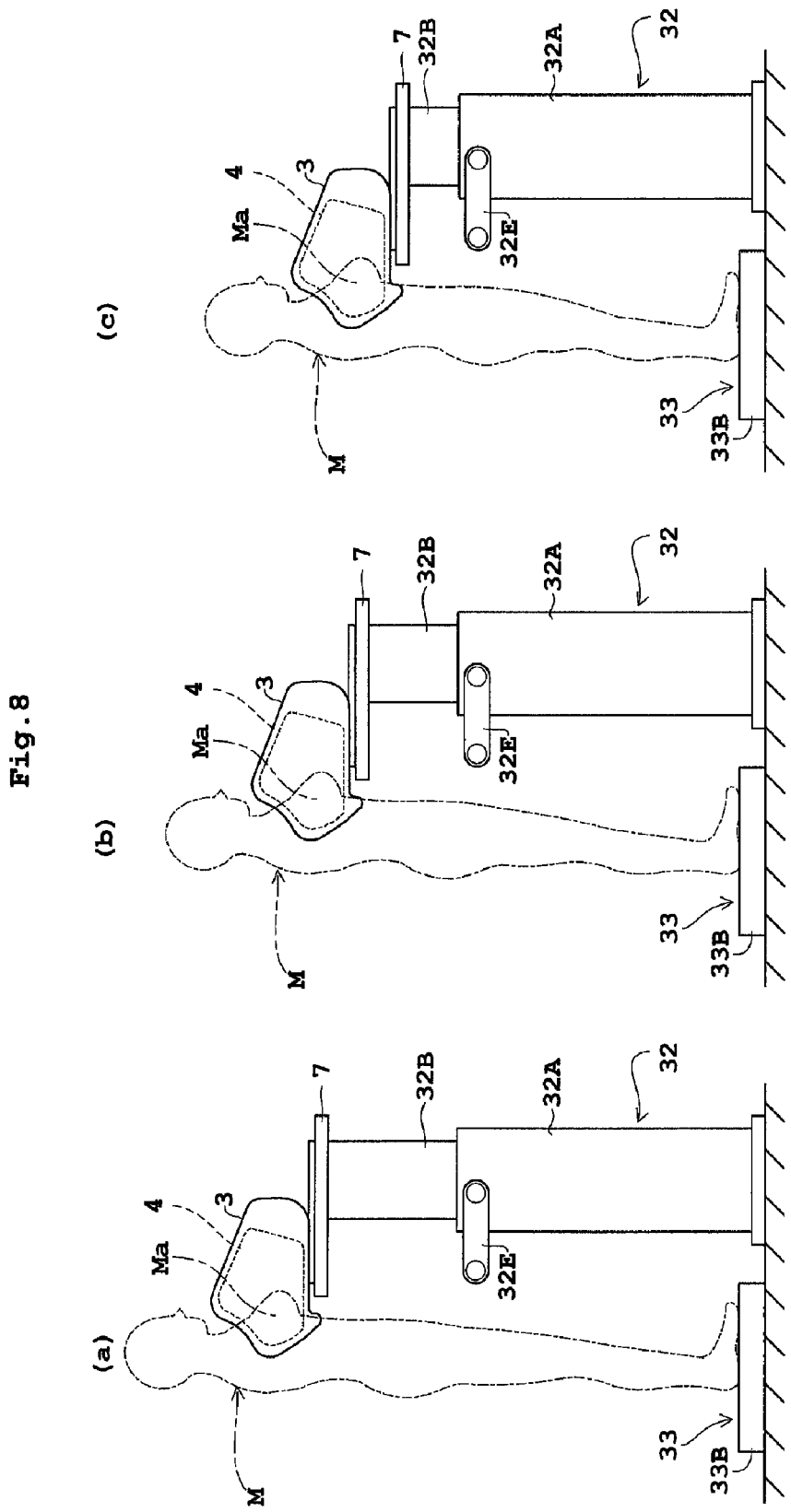
FIGS. 8 (a)-(c) are views showing situations at times of radiography of the apparatus in Embodiment 3 for patients different in size.
Figure 9:
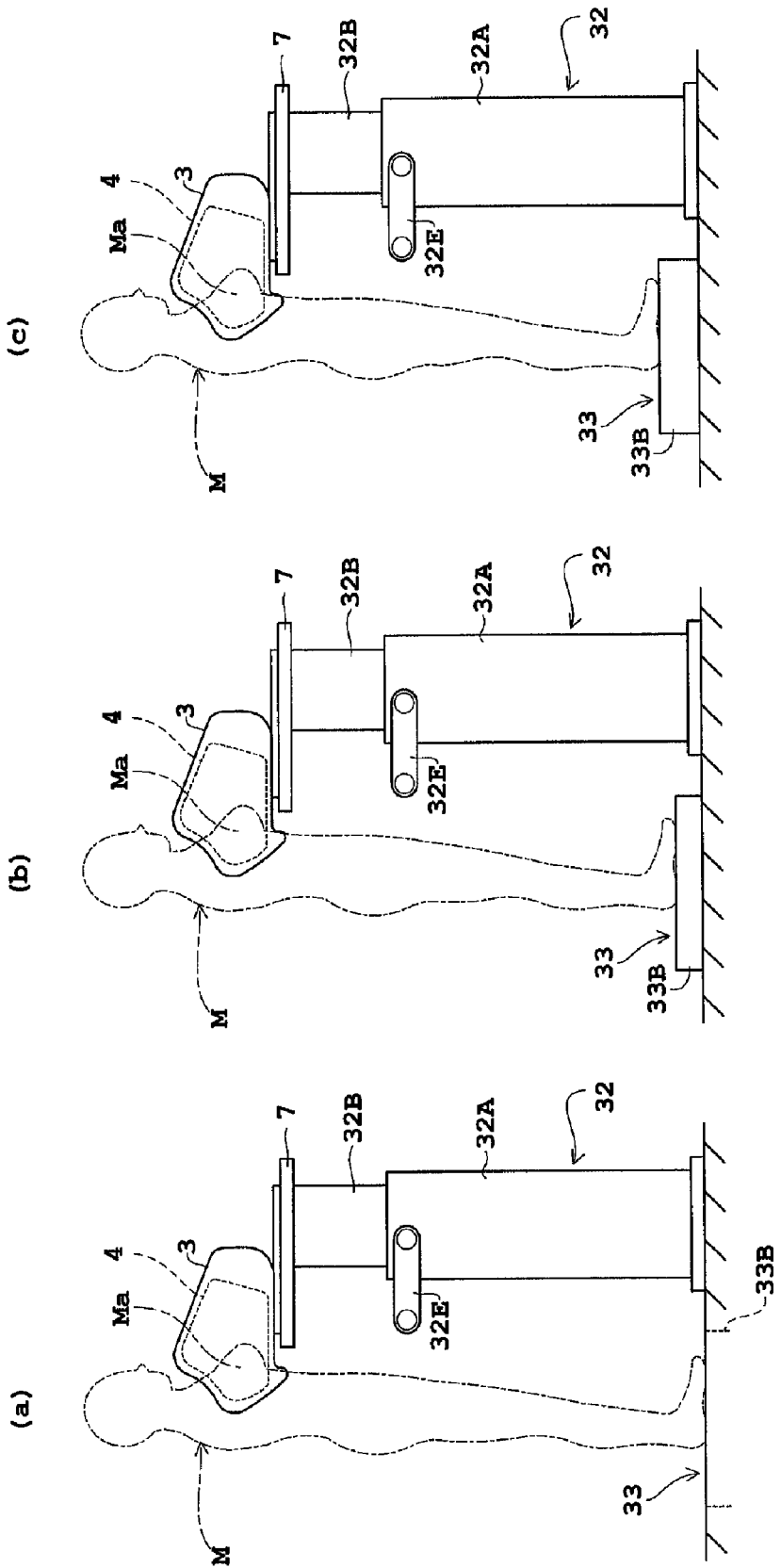
FIGS. 9 (a)-(c) are views showing situations at times of radiography of the apparatus in Embodiment 3 for patients different in size.

When RI distribution images of the breast area Ma of the patient M are photographed with the mammographic apparatus in Embodiment 3, as shown in FIG. 7, the patient M is first set to a standing position or a seated position seated on a wheelchair, next the movable base 32B is moved vertically by the height adjusting mechanism 32, and the sternal plate contact box 3, gamma-ray detector 4 and armrest boards 7 held by the movable base 32B are moved vertically. As shown in FIG. 8, the sternal plate contact box 3, gamma-ray detector 4 and armrest boards 7 are set to a height suited for the physique and photographing posture of the patient M. Alternatively, with the patient M placed on the movable base 33B, the height adjusting mechanism 33 of the platform type vertically moves the movable base 33B, thereby moving the patient M vertically. As shown in FIG. 9, the right and left arms of the patient M are set to the height of the armrest boards 7, and the peripheral portions of the breast area Ma of the sternal plate of the patient M are set in contact with the sternal plate contact box 3.

In the case of the apparatus in Embodiment 3 having the construction described above, as in the apparatus in Embodiments 1 and 2 having the seating unit 2, since the peripheral portions of the breast area Ma of the sternal plate of the patient M are in contact with the sternal plate contact box 3 during radiography for RI distribution images, the motion of the breast area Ma of the patient M accompanying respiration of the patient M is suppressed with ease.

Further, since radiography for RI distribution images is carried out with the patient M in a standing position or a seated position, the apparatus is compact and can be installed in a limited area, compared with an apparatus that carries out radiography for RI distribution images with the patient in a sleeping position lying on the back or on a side on the top board.

Therefore, according to the mammographic apparatus in Embodiment 3, the motion of the breast area Ma accompanying respiration of the patient M can be suppressed easily. In addition, a large installation space is unnecessary.

In the case of the apparatus in Embodiment 3, the height adjusting mechanism 32 holding the sternal plate contact box 3 and gamma-ray detector 4, adjusts their height to the patient's height and photographing posture, with the sternal plate contact box 3 supporting the upper body of the patient M and the gamma-ray detector 4 picking up images of the breast area Ma. The height adjusting mechanism 33 of the platform type moves the patient vertically to adjust the relative height between the sternal plate contact box 3 and gamma-ray detector 4, and the patient M. The sternal plate contact box 3 supports the upper body of the patient M, and the gamma-ray detector 4 picks up images of the breast area Ma. As a result, height adjustment can be carried out according to height differences and photographing postures, to enable an image pick-up suited to the height and photographing posture of each patient M.

Embodiment 4

Embodiment 4 of a mammographic apparatus of this invention will be described with reference to the drawings.

Figure 10:
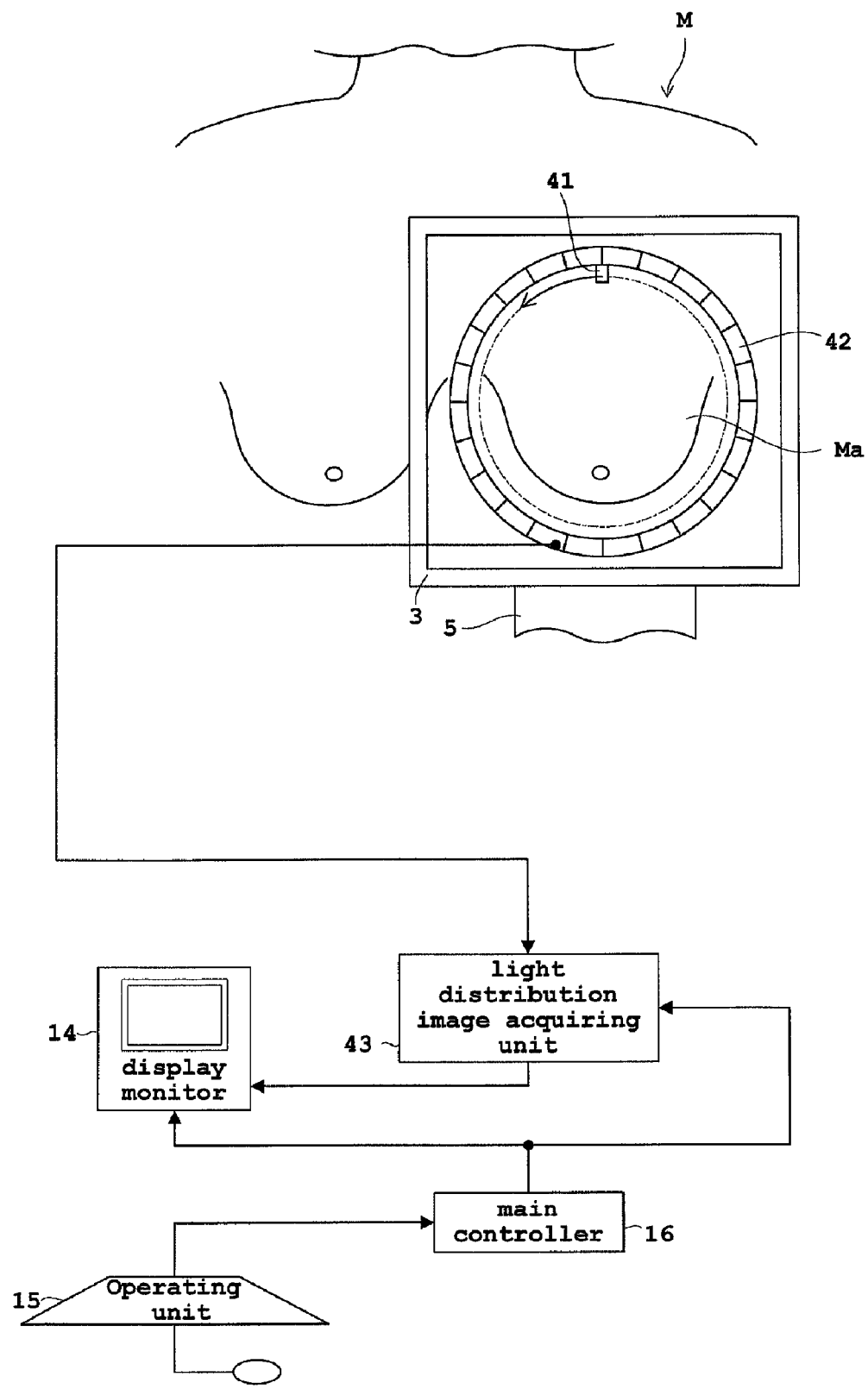
FIG. 10 is a block diagram showing a principal portion of a mammographic apparatus in Embodiment 4.

In the mammographic apparatus in Embodiment 4, instead of detecting gamma rays, collecting emission data and acquiring RI distribution images, as shown in FIG. 10, light is emitted from a light source 41, a light detector 42 detects the light, and a light distribution image acquiring unit 43 acquires light distribution images. The other aspects are substantially the same as in the apparatus in Embodiments 1-3. Only different points will be described, and description of common points will be omitted. The light source 41 corresponds to the light source in this invention. The light detector 42 corresponds to the image pickup device in this invention. The light distribution image acquiring unit 43 corresponds to the light distribution image acquiring device in this invention.

As shown in FIG. 10, the mammographic apparatus in Embodiment 4 includes a same display monitor 14, operating unit 15 and main controller 16 similar to Embodiments 1-3, and in addition, the light source 41 for emitting light to the breast area Ma of the patient M, the light detector 42 for detecting the light emitted from the light source 41, and the light distribution image acquiring unit 43 for obtaining optical images of the breast area Ma of the patient M.

The light source 41 is constructed movable to describe a circumferential track. The light detector 42 carries out optical image pickup by detecting absorption light or fluorescence from the breast area Ma of the patient M irradiated by the light source 41, and outputting photodetection signals. The light detector 42 has a plurality of detecting elements arranged in a concentric circle with the moving track of the light source 41.

According to the photodetection signals outputted from the light detector 42, the light distribution image acquiring unit 43 acquires light distribution images of the breast area Ma of the patient M. Specifically, in optical absorption CT or fluorescence CT, information on light propagation inside the living body is presumed in order to carry out imaging of the density of an internal light-absorbing substance or fluorescent substance based on light information given by detected photodetection signals. The interior of a sample of the living body is divided into minute areas (pixel or voxel), and a sensitivity distribution of each area is determined for a combination of a certain point of emission from the light source 41 and a certain detecting point of the light detector 42. Then, the density of the light-absorbing substance or fluorescent substance in each area is imaged by back projection of detected light information. This imaged data is a light distribution image.

The light source 41 may be a laser or an LED (Light-Emitting Diode) halogen lamp, for example. The light detector 42 may have a function of photoelectric conversion, such as a solid-state image pickup device (CCD), an avalanche photodiode or a photo-multiplier, for example.

In the case of the apparatus in Embodiment 4, the light detector 42 carries out optical image pickup to detect absorption light or fluorescence from the breast area Ma of the patient M irradiated by the light source 41, and output photodetection signals. The light distribution image acquiring unit 43 acquires light distribution images which are optical images of the breast area Ma of the patient M from the photodetection signals outputted from the light detector 42.

The apparatus in Embodiment 4 may be combined with the apparatus in Embodiments 1 and 2, or may be combined with the apparatus in Embodiment 3.

This invention is not limited to the foregoing embodiments, but may be modified as follows:

(1) Although the apparatus in Embodiments 1-4 are mammographic apparatus of the PET type, this invention is applicable also to the types other than PET, such as the SPECT type.

(2) As a modification of the apparatus in Embodiments 1-4, a mammographic apparatus of the X-ray radiographic type may include, instead of the gamma-ray detector, an X-ray image pickup mechanism consisting of an X-ray tube for emitting X rays and a two-dimensional X-ray detector for detecting transmitted X-ray images, with the other components being the same as in the embodiments. The two-dimensional X-ray detector for transmitted X-ray images used in the modified apparatus may be a flat panel X-ray detector or X-ray photo film, for example.

(3) In the apparatus in the embodiments, the sternal plate contact box 3 contacts and supports the peripheral portions of the breast area of the patient's sternal plate. The sternal plate contact device in this invention need not necessarily be box-like, but may be a ring-like member for contacting and supporting the peripheral portions of the breast area. The upper body support device in this invention is not limited to the one that supports the patient's sternal plate, but may be one that contacts and supports the patient's shoulders, for example.

(4) The apparatus in the embodiments have the raising and lowering mechanism for raising and lowering forward and backward relative to the patient. This invention is not limited to this, but the equipment holding arm may be fixedly installed at a predetermined angle of forward inclination.

Figure 11:
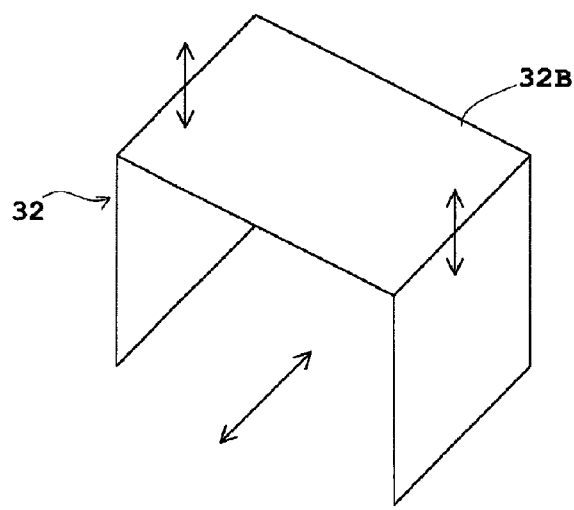
FIG. 11 is a perspective view of a height adjusting mechanism for accommodating a wheelchair.
Figure 12:
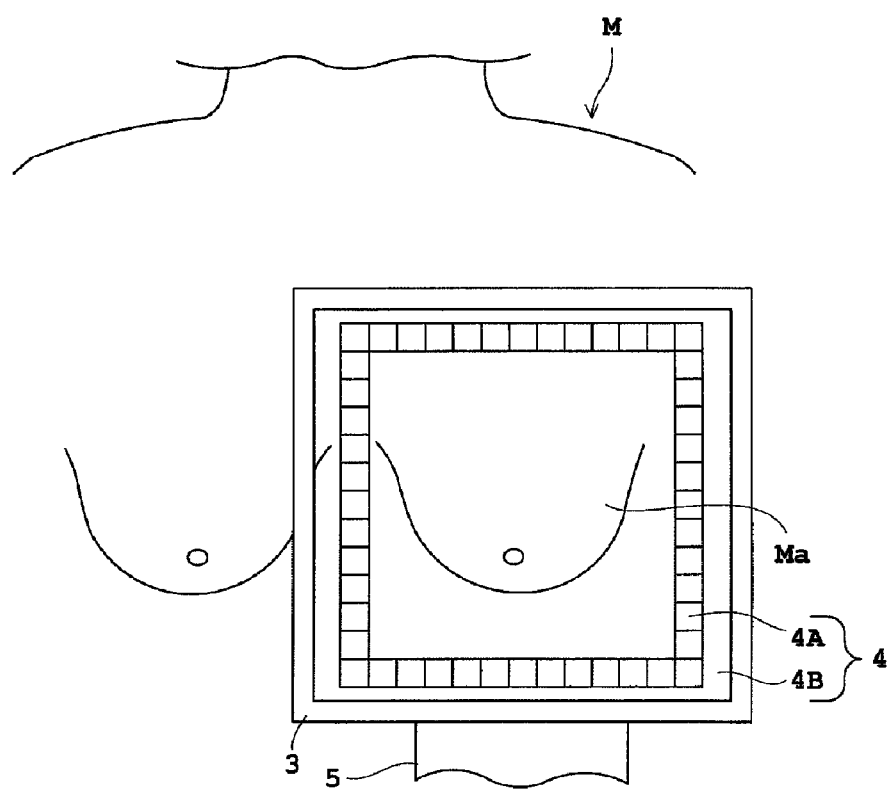
FIG. 12 is a schematic view of a gamma-ray detector of the type that acquires images of right and left individually with one breast received separately.
Figure 13:
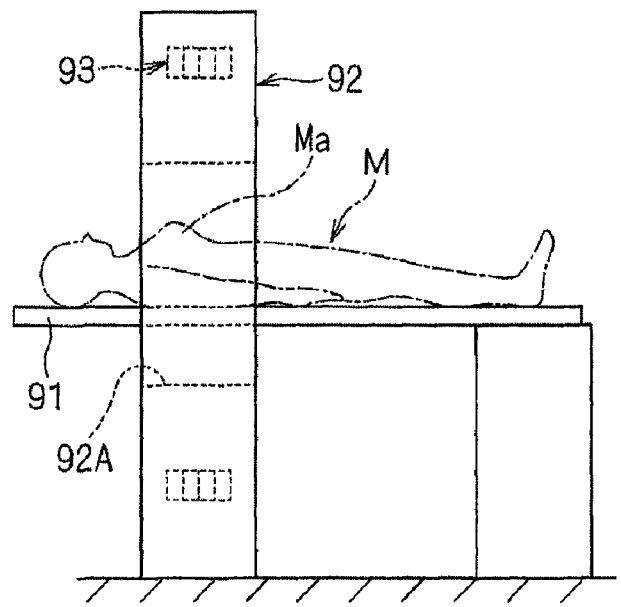
FIG. 13 is an elevational view showing a situation for acquiring images of a patient's breast area with a conventional PET apparatus.
Figure 14:
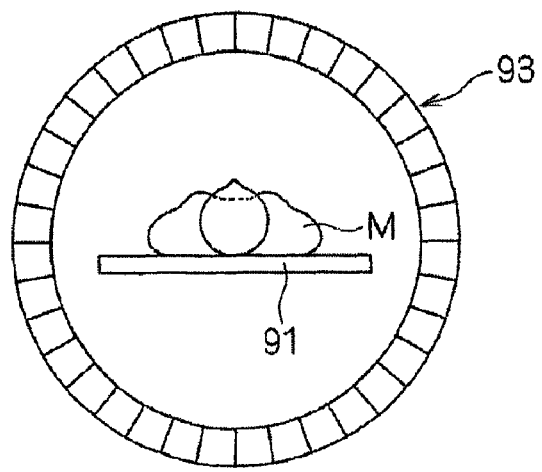
FIG. 14 is a front view showing a construction of a gamma-ray detector of a conventional PET apparatus.
Figure 15:
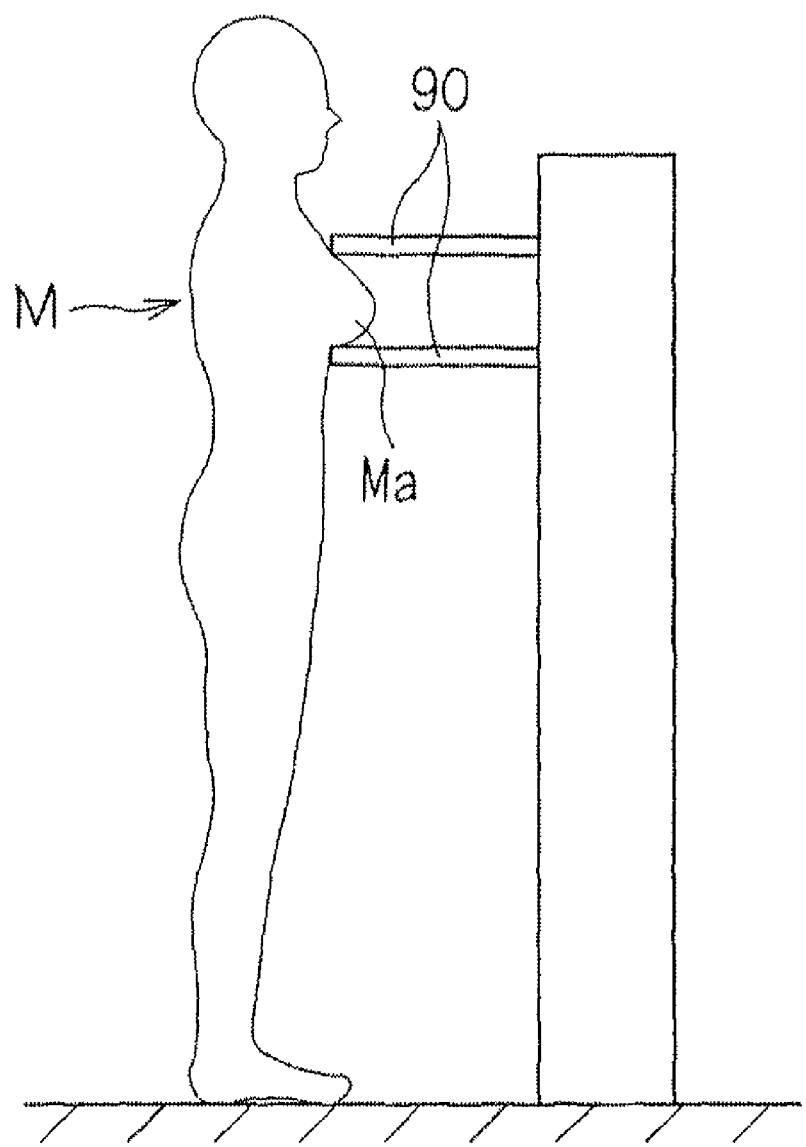
FIG. 15 is an elevational view showing a situation for acquiring patient's breast area with a conventional mammographic apparatus of the X-ray photographing type.

(5) The apparatus in Embodiment 3 has both the height adjusting mechanisms 32 and 33. There is no need to provide both the height adjusting mechanisms 32 and 33, but may provide only one. If height is not taken into consideration, the height adjusting device in this invention is not absolutely necessary. When imaging the breast area Ma of the patient M in the seating position seated on a wheelchair, as shown in FIG. 11, a movable base 32B open in a direction of movement of the wheelchair, with the movable base 32B vertically movable by the height adjusting mechanism 32.

(6) In the apparatus in Embodiments 1-3, as shown in FIG. 2, for example, both breasts are received for simultaneous imaging. In the apparatus in Embodiment 4, as shown also in FIG. 10, one of the breasts is received separately to image the right and left breasts individually. In the apparatus in Embodiments 1-3, as shown in FIG. 11, the image pickup device in this invention (gamma-ray detector 4 in FIG. 11) is applicable to the type that receives one of the breasts separately to image the right and left breasts individually. In the apparatus in Embodiment 4, the image pickup device in this invention is applicable to the type that receives both breasts for simultaneous imaging. Thus, the image pickup device is applicable to both of the type that receives both breasts for simultaneous imaging and the type that receives one of the breasts separately to image the right and left breasts individually.

The invention claimed is:

1. A mammographic apparatus for imaging a patient's breast area, comprising (A) a seating device for seating the patient; (B) an upper body support device for supporting the weight associated with an upper body of the patient seated on the seating device; and (C) an image pickup device for picking up images of the breast area of the patient seated on the seating device and having the upper body supported by the upper body support device, wherein the upper body support device contacts and supports the peripheral portions of the breasts, wherein the upper body support device is a sternal plate contact device contactable by one of peripheral portions of the breast area of the patient's sternal plate, and wherein the image pickup device is a gamma-ray detector for receiving the patient's breast area and carrying out radiation image pickup by detecting gamma rays produced by a radioisotope introduced into the patient and having reached the breast area, and outputting gamma ray detection signals, said apparatus further comprising (I) an emission data collecting device for collecting emission data for RI distribution image acquisition according to the gamma ray detection signals outputted from the gamma-ray detector, and (J) an RI distribution image acquiring device for acquiring RI distribution images which are radiographic images of the patient's breast area based on the emission data collected by the emission data collecting device.

2. The mammographic apparatus according to claim 1 further comprising (D) an equipment holding device for holding the upper body support device and the image pickup device; and (E) as raising and lowering device for raising and lowering the equipment holding device together with the upper body support device and the image pickup device, forward and backward relative to the patient.

3. The mammographic apparatus according to claim 2, further comprising (G) a lower leg contact device held by the equipment holding device to be contactable by lower legs of the patient seated on the seating device.

4. The mammographic apparatus according to claim 1, further comprising (F) an armrest device arranged laterally of the sternal plate contact device for receiving right and left arms of the patient.

5. The mammographic apparatus according to claim 4, further comprising (D) an equipment holding device for holding the upper body support device and the image pickup device; and (E) a raising and lowering device for raising and lowering the equipment holding device together with the upper body support device and the image pickup device, forward and backward relative to the patient, the seating device also being held by the equipment holding device, said apparatus further comprising (H) a tilt avoiding device for avoiding tilting of the armrest device by raising and lowering the armrest device in an opposite direction in response to raising, and lowering, of the equipment holding device.

6. The mammographic apparatus according to claim 1, wherein the radioisotope is a positron type radioisotope, the emission data collecting device collecting the emission data according to the gamma ray detection signals when annihilation gamma rays moving in opposite directions are simultaneously detected by the gamma-ray detector.

7. The mammographic apparatus according to any one of claims 1, 2, and 4 to 5, wherein the image pickup device receives both of breasts, and picks up images thereof simultaneously.

8. The mammographic apparatus according to any one of claims 1, 2, and 4 to 5, wherein the image pickup device receives one breast separately, and picks up images right and left breasts individually.

9. A mammographic apparatus for imaging a patient's breast area, comprising (A) a seating device for seating the patient; (B) an upper body support device for supporting the weight associated with an upper body of the patient seated on the seating device; (C) an image pickup device for picking up images of the breast area of the patient seated on the seating device and having the upper body supported by the upper body support device; and (K) a light source for emitting light to the patient's breast area, wherein the image pickup device is a light detector for carrying out optical image pickup by detecting absorption light or fluorescence from the patient's breast area irradiated by the light source, and outputting photodetection signals, said apparatus further comprising (L) a light distribution image acquiring device for acquiring light distribution images which are optical images of the patient's breast area according to the photodetection signals outputted from the light detector, wherein the upper body support device contacts and supports the peripheral portions of the breasts, and wherein the upper body support device is a sternal plate contact device contactable by one of peripheral portions of the breast area of the patient's sternal plate.

10. The mammographic apparatus according to claim 9, further comprising (D) an equipment holding device for holding the upper body support device and the image pickup device; and (E) a raising and lowering device for raising and lowering the equipment holding device together with the upper body support device and the image pickup device, forward and backward relative to the patient.

11. The mammographic apparatus according to claim 10, further comprising (G) a lower leg contact device held by the equipment holding device to the contactable by lower legs of the patient seated on the seating device.

12. The mammographic apparatus according to claim 9, further comprising (F) an armrest device arranged laterally of the sternal plate contact device for receiving right and left arms of the patient.

13. The mammographic apparatus according to claim 12, further comprising (D) an equipment holding device for holding the upper body support device and the image pickup device; and (E) a raising and lowering device for raising and lowering the equipment holding device together with the upper body support device and the image pickup device, forward and backward relative to the patient, the seating device also being held by the equipment holding device, said apparatus further comprising (H) a tilt avoiding device for avoiding tilting of the armrest device by raising and lowering the armrest device in an opposite direction in response to raising and lowering of the equipment holding device.

14. The mammographic apparatus according to any one of claims 9 and 10 to 13, wherein the image pickup device receives both of breasts, and picks up images thereof simultaneously.

15. The mammographic apparatus according to any one of claims 9 and 10 to 13, wherein the image pickup device receives one breast separately, and picks up images right and left breasts individually.

16. A mammographic apparatus for imaging a patient's breast area, comprising (b) an upper body support device for supporting the weight associated with an upper body of a patient in a standing or seated position, and (c) an image pickup device for picking up images of the breast area of the patient in the standing, or seated position and having the upper body supported by the upper body support device, wherein the upper body support device contacts and supports the peripheral portions of the breasts, wherein the upper body support device is a sternal plate contact device contactable by one of peripheral portions of the breast area of the patient's sternal plate, and wherein the image pickup device is a gamma-ray detector for receiving the patient's breast area and carrying out radiation image pickup by detecting gamma rays produced by a radioisotope introduced into the patient and having reached the breast area, and outputting gamma ray detection signals, said apparatus further comprising (i) an emission data collecting device for collecting emission data for RI distribution image acquisition according to the gamma ray detection signals outputted from the gamma-ray detector, and (j) an RI distribution image acquiring device for acquiring RI distribution images which are radiographic images of the patient's breast area based on the emission data collected by the emission data collecting device.

17. The mammographic apparatus according to claim 16, further comprising (d) a height adjusting device for holding the upper body support device and the image pickup device and adjusting a height thereof, or for vertically moving the patient to adjust a relative height between the upper body support device and the image pickup device, and the patient.

18. The mammographic apparatus according to claim 16, further comprising (f) an armrest device arranged laterally of the sternal plate contact device for receiving right and left arms of the patient.

19. The mammographic apparatus according to claim 16, wherein the radioisotope is a positron type radioisotope, the emission data collecting device collecting the emission data according to the gamma ray detection signals when annihilation gamma rays moving in opposite directions are simultaneously detected by the gamma-ray detector.

20. The mammographic apparatus according to any one of claims 16, 17, and 18, wherein the image pickup device receives both of breasts, and picks up images thereof simultaneously.

21. mammographic apparatus according to any one of claims 16, 17, and 18, wherein receives one breast separately, and picks up images right and left breasts individually.

22. A mammographic apparatus for imaging a patient's breast area, comprising (b) an upper body support device for supporting the weight associated with an upper body of a patient in a standing or seated position; (c) an image pickup device for picking up images of the breast area of the patient in the standing or seated position and having the upper body supported by the upper body support device; and (k) a light source for emitting light to the patient's breast area, wherein the image pickup device is a light detector for carrying out optical image pickup by detecting absorption light or fluorescence from the patient's breast area irradiated by the light source, and outputting photodetection signals, said apparatus further comprising (l) a light distribution image acquiring device for acquiring light distribution images which are optical images of the patient's breast area according to the photodetection signals outputted from the light detector, wherein the upper body support device contacts and supports the peripheral portions of the breasts, and wherein the upper body support device is a sternal plate contact device contactable by one of peripheral portions of the breast area of the patient's sternal plate.

23. The mammographic apparatus according to claim 22, further comprising (d) a height adjusting device for holding the upper body support device and the image pickup device and adjusting a height thereof, or for vertically moving the patient to adjust a relative height between the upper body support device and the image pickup device, and the patient.

24. The mammographic apparatus according to claim 22, further comprising (f) an armrest device arranged laterally of the sternal plate contact device for receiving right and left arms of the patient.

* * * * *